United States Patent

Benedetti et al.

[11] Patent Number: 6,022,965
[45] Date of Patent: Feb. 8, 2000

[54] METHOD FOR ISOMERISING THE 10-METHYL RADICAL OF ERYTHROMYCIN DERIVATIVES

[75] Inventors: Yannick Benedetti, Rosny sous Bois; Jacques Lagouardat, Noisy le Grand; Jacques Scholl, Romainville, all of France

[73] Assignee: Hoechst Marion Roussel, France

[21] Appl. No.: 09/180,641

[22] PCT Filed: May 13, 1997

[86] PCT No.: PCT/FR97/00840

§ 371 Date: Nov. 11, 1998

§ 102(e) Date: Nov. 11, 1998

[87] PCT Pub. No.: WO97/43297

PCT Pub. Date: Nov. 20, 1997

[30] Foreign Application Priority Data

May 14, 1996 [FR] France ................................ 96 05966

[51] Int. Cl.[7] .................................................. C07H 1/00
[52] U.S. Cl. ........................ 536/125; 536/7.4; 536/18.5
[58] Field of Search ........................... 536/7.2, 7.9, 18.5, 536/12.5; 514/29

[56] References Cited

FOREIGN PATENT DOCUMENTS 0676409  10/1995  European Pat. Off. .

*Primary Examiner*—Elli Peselev
*Attorney, Agent, or Firm*—Bierman, Muserlian and Lucas

[57] ABSTRACT

An isomerization method wherein a compound of formula

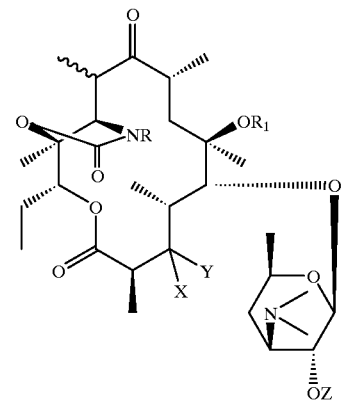

IA wherein X and y together form a 3-oxo radical, or X is a hydrogen atom and Y is either a radical a

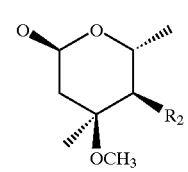

a where $R_2$ is OH or O-acyl, or an O-alkyl or $NH_2$ radical; $R_1$ is a hydrogen atom or a methyl radical; Z is hydrogen or an acyl radical; and R is a hydrogen atom, an $NH_2$ radical or a $(CH_2)_n Ar$, $NH(CH_2)_n Ar$ or $N=CH(CH_2)_n Ar$ radical, in the form of a 10α isomer or a mixture of 10α and 10β isomers, is exposed to a basic agent to give the corresponding compound of formula I in which the 10-methyl radical is in the β position.

10 Claims, No Drawings

METHOD FOR ISOMERISING THE 10-METHYL RADICAL OF ERYTHROMYCIN DERIVATIVES

This application is a 371 of PCT/FR97/00840, filed May 13, 1997.

The invention relates to a new isomerization process for the methyl radical at 10 of erythromycin derivatives A subject of the invention is an isomerization process characterized in that a compound of formula ($I_A$):

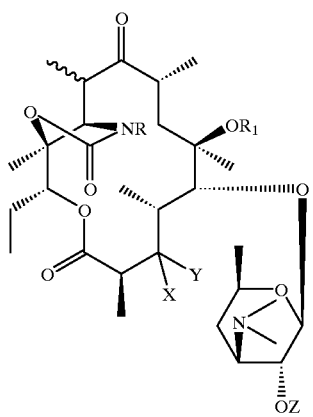

(I_A)

in which either X and Y form together a 3-oxo radical, or X represents a hydrogen atom and Y represents either a radical:

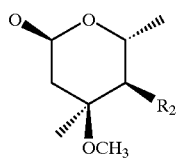

in which $R_2$ represents a hydroxyl radical or an O-acyl radical containing from 2 to 20 carbon atoms, or an O-alkyl radical, containing from 2 to 20 carbon atoms, or an $NH_2$ radical, $R_1$ represents a hydrogen atom or a methyl radical, Z represents a hydrogen or an acyl radical containing from 2 to 20 carbon atoms, R represents a hydrogen atom, an $NH_2$ radical or a $(CH_2)_n Ar$, $NH(CH_2)_n Ar$ or $N=CH(CH_2)_n Ar$ radical in which n represents an integer comprised between 1 and 6, and Ar represents an optionally substituted aryl or heteroaryl radical, in the form of the 10α isomer or a mixture of 10α and 10β isomers, is subjected to the action of a basic agent in order to obtain the corresponding compound of formula (I) in which the methyl radical at 10 is in the β position:

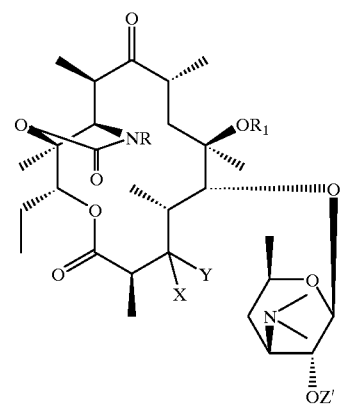

(I)

and in which R, $R_1$, X and Y retain their previous meaning and Z' represents a hydrogen atom or an acyl radical containing from 2 to 20 carbon atoms. The acyl radical is preferably an acetyl, propionyl, butyryl, isobutyryl, n-valeryl, isovaleryl, tervaleryl and pivalyl radical, or a benzyl radical. By aryl radical, is preferably meant a phenyl or naphthyl radical, by heteroaryl radical, is meant a radical containing one or more heteroatoms preferably chosen from oxygen, sulphur or nitrogen, it can be one of the following radicals: thienyl, furyl, pyrrolyl, thiazolyl, oxazolyl, imidazolyl, thiadiazolyl, pyrazolyl, or isoxazolyl, a pyridyl, pyridazinyl, or pyrazinyl radical, an indolyl, benzofuryl, benzothienyl, quinolinyl or pyridyl-imidazolyl radical. As heteroaryl radical, there can be mentioned for example the radicals:

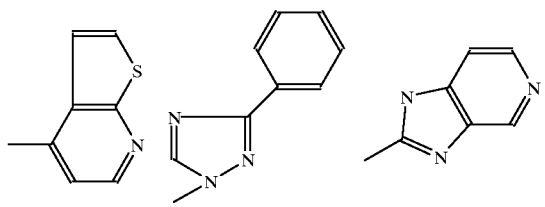

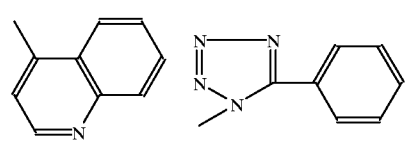

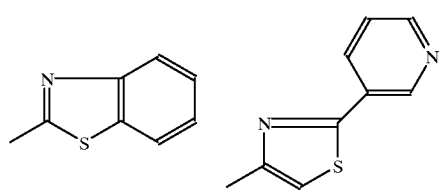

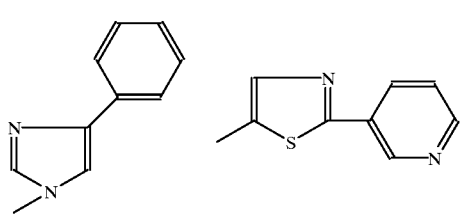

-continued

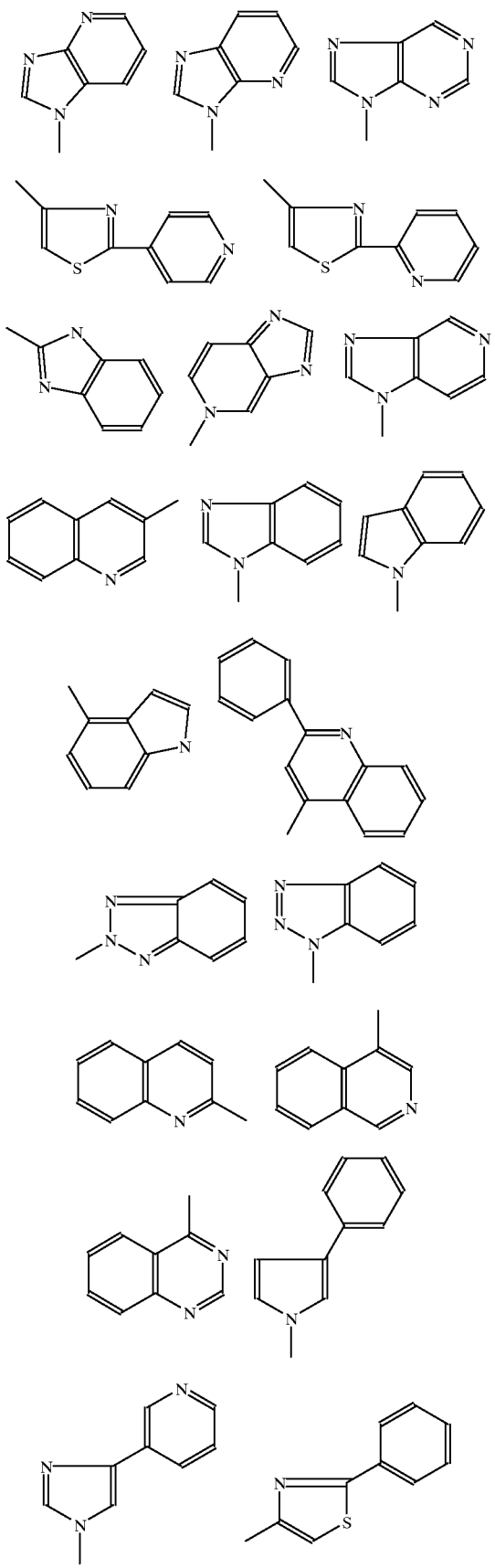

-continued

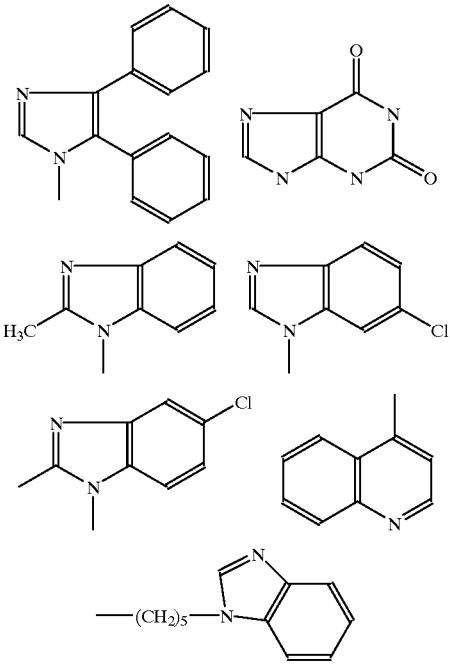

A more particular subject of the invention is a process characterized in that the operation is carried out in the presence of a basic agent, preferably in a catalytic quantity, Z and Z' representing a hydrogen atom. The basic agent is preferably potash or also a tetraalkylammonium hydroxide for example tetrabutylammonium hydroxide or bromide or DBU (1,8-diazabicyclo [5-4-0]undec-7-ene) or an alkaline carbonate for example sodium or potassium carbonate or soda or tripotassium phosphate or also sodium methylate.

It may be necessary in certain cases to add a phase transfer agent, for example tetrabutyl ammonium bromide.

A quite particular subject of the invention is a process characterized in that the operation is carried out in a solvent which can be for example tetrahydrofuran, 1-methyl 2-pyrrolidonone in aqueous solution, methylene chloride and more particularly an alcohol in particular methanol and in this way the corresponding compound in which Z' represents a hydrogen atom, or an acyl radical containing from 2 to 20 carbon atoms is obtained.

A more particular subject of the invention is:

a process for isomerizing the compounds of formula ($I_A$) into (I) in which R represents an $NH_2$ radical, a process for isomerizing the compounds of formula ($I_A$) into (I) in which $R_1$ represents a methyl radical, a process for isomerizing the compounds of formula ($I_A$) into (I), characterized in that X and Y form together a 3-oxo radical, a process for isomerizing the compounds of formula ($I_A$) into (I) in which Z and Z' represent a hydrogen atom.

Therefore, the invention relates to a process which allows the conversion of compounds of formula ($I_A$) in which the methyl radical at 10 is in the α position or a mixture of 10α and 10β into the compounds of formula (I) in which the methyl radical at 10 is in the 10β position. During the formation of the chain in the 11, 12 position a mixture of 10α and 10β isomers is obtained, therefore if the process described in the Patent EP 676409 is followed, the following reaction is obtained:

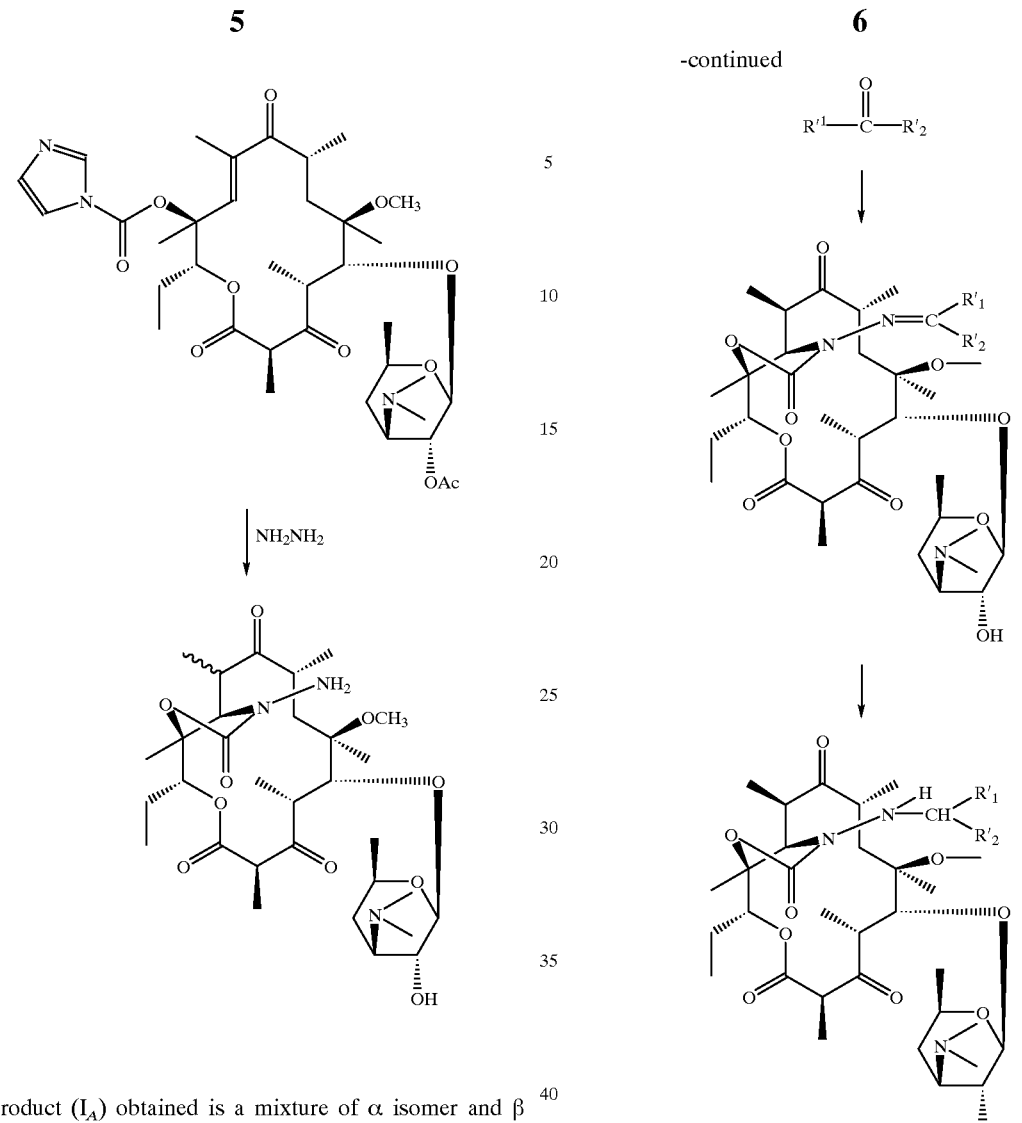

the product ($I_A$) obtained is a mixture of α isomer and β isomer, as indicated in Example 1 of the Patent EP 676409. The 10β product is a product endowed with useful antibiotic properties, it also allows the preparation of other antibiotic products described and claimed in the Patent Application 676409 according to the process:

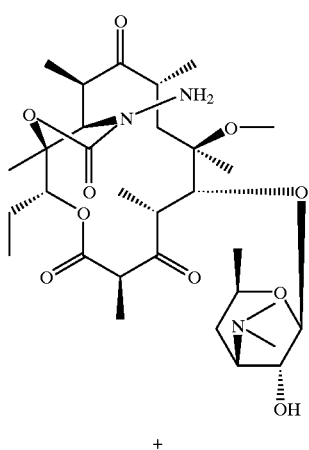

+

The compounds endowed with useful antibiotic properties are those in which the methyl radical at 10 is in the β position. It is therefore useful from an industrial point of view to isomerize the 10α product or 10α and 10β mixtures into the 10β product. The process according to the invention in particular allows the isomerization into the 10β isomer of the products of formula ($I_A$) in which R is an $NH_2$ radical, those in which R is a hydrogen atom, or also those in which R is a $(CH_2)_nAr$, $NH—(CH_2)_nAr$ or $N=CH(CH_2)_nAr$ radical in which n and Ar retain their previous meaning.

These products are described for example in the Patent Applications EP 676409, EP 638584, EP 680967, EP 0596802, EP 487411.

The following examples illustrate the invention without however limiting it.

EXAMPLE 1

0.1 g of the 10α isomer of 11,12-dideoxy 3-de-((2,6-dideoxy 3-C-methyl 3-O-methyl alpha L-ribohexopyranosyl)oxy) 6-O-methyl 3-oxo 12,11-(oxycarbonyl(hydrozono)erythromycin (prepared as indicated in the European Patent Application 0676409, product B 10S isomers) is dissolved in 2 ml of methanol and 10 μl of a 10% solution of methanolic potash is added. Agitation is carried out overnight a 20° C. and the formation of the 10β isomer is observed. This 10β isomer is characterized by its NMR spectrum.

The isomerization yield is of the order of 90%.

By operating as in Example 1, the 10β isomer of the product of Example 1 was obtained, starting from 0.5 g of the 10α product:

methanol 10 volumes; 0.11 ml of a 10% solution of potash in methanol, methanol 10 volumes; 26 µl of a 40% solution of tetrabutylammonium hydroxide in water, methanol 10 volumes; 0.13 ml of a 40% solution of tetrabutylammonium hydroxide in water, methanol with 20% water 10 volumes; 0.11 ml of a 10% solution of KOH in methanol, methanol with 20% water 10 volumes; 26 µl of a 40% solution of tetrabutylammonium hydroxide in water, methanol with 20% water 10 volumes; 0.13 ml of a 40% solution of tetrabutylammonium hydroxide in water, methanol with 20% water 10 volumes; DBU 30 µl.

EXAMPLE 2

Starting from a mixture of α+β isomers

The following are introduced into a 1000 ml three-necked flask provided with agitation, a thermometer probe and a sweeping nitrogen supply:

a mixture of α and β isomers 37.8 g (α isomer=15.8 g; β isomers=22 g) 11,12-dideoxy 3-de-((2,6-dideoxy 3-C-methyl 3-O-methylαL-ribohexopyranosyl)oxy) 6-O-methyl 3-oxo 12,11-(oxycarbonyl)hydrazono) erythromycin (α isomer=15.8 g: β isomer=22 g)

pure anhydrous methanol

10% methanolic potash

The reaction medium is maintained under agitation for 20 hours at 20~22° C.

The disappearance of the 10α isomer (<2%) is verified by HPLC then:

demineralized water is introduced while controlling the temperature at 20/22° C. using an ice+water bath, the pH is adjusted to 10 with acetic acid qs (~0.250 ml), agitation is carried out for 3 hours at 20/22° C., followed by cooling down to 0+2° C., agitation is carried out for 1 hour at 0°+2° C., followed by separation by clarification using:

demineralized water at 20° C.

Drying in a ventilated oven at 30° C. for 16 hours.

The pure β isomer is recovered: 32.6 g.

Yield : 86.2% relative to the α and β mixture.

EXAMPLE 3

0.2 g of a mixture of 10α and 10β isomers of 11,12-dideoxy 3-de-((2,6-dideoxy 3-C-methyl 3-O-methylαL-ribohexopyranosyl)oxy) 6-O-methyl 3-oxo 12,11-(oxycarbonyl)hydrazono)erythromycin (% β/% α=0.24) is dissolved in 1 ml of methanol and 50 µl of a 10% solution of methanolic potash is added. Agitation is carried out for 16 hours at 20° C. and the conversion of the 10α isomer into the 10β isomer is observed. (% β/% α=21).

EXAMPLE 4

0.1 g of a mixture of 10α and 10β isomers of 11,12-dideoxy 3-de-((2,6-dideoxy 3-C-methyl 3-O-methylαL-ribohexopyranosyl)oxy) 6-O-methyl 3-oxo 12,11-(oxycarbonyl)hydrazono)erythromycin (% β/% α=0.24) is dissolved in 0.5 ml of methanol and 0.25 mole per mole of (1,8- diazabicyclo [5-4-0]undec-7-ene is added. Agitation is carried out for 16 hours at 20° C. and the conversion of the 10α isomer into the 10β isomer is observed. (% β/% α=16.3).

EXAMPLE 5

0.1 g of a mixture of 10α and 10β isomers of 11,12-dideoxy 3-de-((2,6-dideoxy 3-C-methyl 3-O-methylαL-ribohexopyranosyl)oxy) 6-O-methyl 3-oxo 12,11-(oxycarbonyl)hydrazono)erythromycin (% β/% α=0.24) is dissolved in 0.5 ml of dichioromethane and 1 mole per mole of (1,8-diazabicyclo [5-4-0]undec-7-ene is added. Agitation is carried out for 16 hours at 20° C. and the conversion of the 10α isomer into the 10β isomer is observed. (% β/% α=2.6).

EXAMPLE 6

0.1 g of a mixture of 10α and 10β isomers of 11,12-dideoxy 3-de-((2,6-dideoxy 3-C-methyl 3-O-methylαL-ribohexopyranosyl)oxy) 6-O-methyl 3-oxo 12,11-(oxycarbonyl)hydrazono)erythromycin (% β/% α=0.24) is dissolved in 2 ml of methanol and 1 mole per mole of potassium carbonate is added. Agitation is carried out for 16 hours at 20° C. and the conversion of the 10α isomer into the 10β isomer is observed. (% β/% α=49).

EXAMPLE 7

0.1 g of a mixture of 10α and 10β isomers of 11,12-dideoxy 3-de((2,6-dideoxy 3-C-methyl 3-O-methylαL-ribohexopyranosyl)oxy) 6-O-methyl 3-oxo 12,11-(oxycarbonyl)hydrazono)erythromycin (% β/% α=0.24) is dissolved in 2 ml of methanol and 1 mole per mole de potassium phosphate is added. Agitation is carried out for 16 hours at 20° C. and the conversion of the 10α isomer into the 10β isomer is observed. (% β/% α=10.2).

EXAMPLE 8

0.1 g of a mixture of 10α and 10β isomers of 11,12-dideoxy 3-de-((2,6-dideoxy 3-C-methyl 3-O-methylαL-ribohexopyranosyl)oxy) 6-O-methyl 3-oxo 12,11-(oxycarbonyl)hydrazono)erythromycin (% β/% α=0.24) is dissolved in 2 ml of methanol and 0.2 mole per mole of sodium carbonate and 0.2 mole per mole of tetrabutylammonium bromide are added. Agitation is carried out for 16 hours at 20° C. and the conversion of the 10α isomer into the 10β isomer is observed. (%β/% α=80).

EXAMPLE 9

0.1 g of a mixture of 10α and 10β isomers of 11,12-dideoxy 3-de-((2,6-dideoxy 3-C-methyl 3-O-methylαL-ribohexopyranosyl)oxy) 6-O-methyl 3-oxo 12,11-(oxycarbonyl)hydrazono)erythromycin (% β/% α=0.24) is dissolved in 0.5 ml of methanol and 33 µl of a solution of sodium methylate in methanol at 5 g % ml is added. Agitation is carried out for 16 hours at 20° C. and the conversion of the 10α isomer into the 10β isomer is observed. (% β/% α=0. EXAMPLE 6: 0.1 g of a mixture of 10α and 10β isomers of 11,12-dideoxy 3-de-((2,6-dideoxy 3-C-methyl 3-O-methylαL-ribohexopyranosyl)oxy) 6-O-methyl 3-oxo 12,11-(oxycarbonyl)hydrazono)erythromycin (% β/% α=0.24) is dissolved in 0.5 ml of methanol and 1 mole per mole of potassium carbonate is added. Agitation is carried out for 16 hours at 20° C. and the conversion of the 10α isomer into the 10β isomer is observed. (% β/% α=0.7).

We claim:

1. An isomerization process for the preparation of a compound of the formula

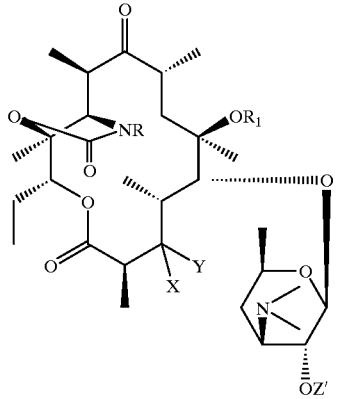

I with the 10-methyl in the beta position wherein $R_1$ is hydrogen or methyl, $R_2$ is selected from the group consisting of —OH, acyloxy of organic carboxylic acid of 2 to 20 carbon atoms, alkoxy of 2 to 20 carbon atoms and —$NH_2$, X and Y form =O or X is hydrogen and Y is

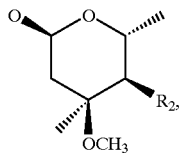

Z' is hydrogen or acyl of an organic carboxylic acid of 2 to 20 carbon atoms and R is selected from the group consisting of hydrogen, —$NH_2$, —$(CH_2)_n$—Ar, —NH—$(CH_2)_n$—Ar and —N=CH—$(CH_2)_n$—Ar, N is an integer from 1 to 6 and Ar is optionally substituted aryl or heteroaryl comprising reacting a compound of the formula

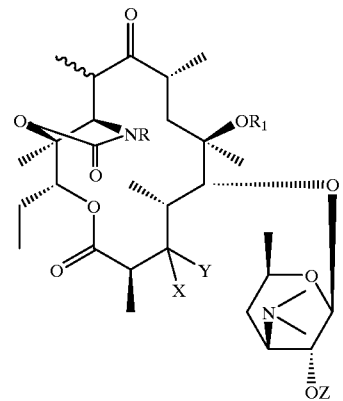

IA in the 10α-isomer or a mixture of 10α- and 10β-isomers wherein Z is hydrogen or acyl of an organic carboxylic acid of 2 to 20 carbon atoms with a basic agent to obtain the 10β-methyl isomer of formula I.

2. The process of claim 1 wherein Z and Z' are hydrogen.

3. The process of claim 1 wherein the basic agent is potassium hydroxide.

4. The process of claim 1 wherein the basic agent is selected from the group consisting of tetrabutylammonium hydroxide or bromide, an alkali metal carbonate sodium hydroxide, (1,8-diazabicyclo[5-4-0]undec7-ene), tripotassium phosphate and sodium methylate.

5. The process of claim 1 wherein the operation is carried out in a solvent selected from the group consisting of tetrahydrofuran, 1-methyl-2-pyrrolidinone in aqueous solution, methylene chloride and an alcohol and Z' is hydrogen or an acyl of an organic carboxylic acid of 2 to 20 carbon atoms.

6. The process of claim 5 wherein the solvent is a methanolic solution.

7. The process of claim 1 wherein R is $NH_2$.

8. The process of claim 1 wherein $R_1$ is methyl.

9. The process of claim 1 wherein X and Y are =O.

10. The process of claim 1 wherein Z and Z' are hydrogen.

* * * * *